United States Patent

Chiang

[11] Patent Number: 5,849,932
[45] Date of Patent: Dec. 15, 1998

[54] BISMALEIMIDE COMPOUND AND PROCESS FOR PRODUCING THE SAME

[75] Inventor: Lin-chiu Chiang, Kitaibaraki, Japan

[73] Assignee: Nippon Mektron, Limited, Tokyo, Japan

[21] Appl. No.: 805,523

[22] Filed: Feb. 26, 1997

[30] Foreign Application Priority Data

Mar. 14, 1996 [JP] Japan .................................. 8-085720

[51] Int. Cl.$^6$ ................................................ C07D 403/08
[52] U.S. Cl. ........................................... 548/522; 548/521
[58] Field of Search ...................... 548/521, 522

[56] References Cited

U.S. PATENT DOCUMENTS

| | | | |
|---|---|---|---|
| 2,444,536 | 6/1948 | Searle | 548/521 X |
| 3,018,290 | 1/1962 | Sauers et al. | 548/522 |
| 3,839,358 | 10/1974 | Bargain | 548/522 X |
| 4,130,564 | 12/1978 | Haug et al. | 548/522 |
| 4,138,406 | 2/1979 | Balasfalvy | 548/522 |
| 4,229,351 | 10/1980 | Kiefer et al. | 548/522 |
| 5,610,240 | 3/1997 | Hoght et al. | 525/332.6 |

OTHER PUBLICATIONS

Galanti et al., J. Polym. Sci., Polymer Chemistry Edition, 20, 233–239 (1982).

*Primary Examiner*—Fiona T. Powers
*Attorney, Agent, or Firm*—Kenyon & Kenyon

[57] ABSTRACT

A novel bismaleimide compound having the following formula:

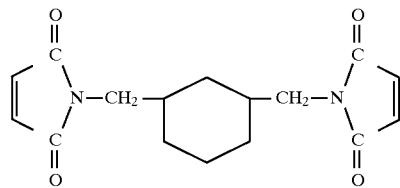

is synthesized from 1,3-bis(aminomethyl)cyclohexane and maleic anhydride, and is readily soluble in a variety of ordinary low boiling point organic solvents.

4 Claims, No Drawings

BISMALEIMIDE COMPOUND AND PROCESS FOR PRODUCING THE SAME

BACKGROUND OF THE INVENTION

1. Field of the Invention

The present invention relates to a bismaleimide compound and a process for producing the same, and more particularly to a novel bismaleimide compound effectively applicable to the production of heat-resistant polymers and a process for producing the same.

2. Related Prior Art

Compounds having an imide structure in the molecule have so far had disadvantages of being substantially insoluble in ordinary organic solvents and being soluble only in specific high boiling point, aprotic polar solvents such as N-methyl-2-pyrrolidone, dimethyl acetamide, etc. Accordingly, when impregnant varnishes prepared by dissolving the compounds in these specific solvents are applied, a high temperature is required for removing the solvents and the solvents are liable to remain in the prepregs formed from the varnishes, causing foaming in the laminates and considerably lowering the quality of FPC (flexible printed circuits).

SUMMARY OF THE INVENTION

An object of the present invention is to provide a novel bismaleimide compound readily soluble in a variety of ordinary low boiling point organic solvents.

According to the present invention, there is provided a novel bismaleimide compound represented by the following formula:

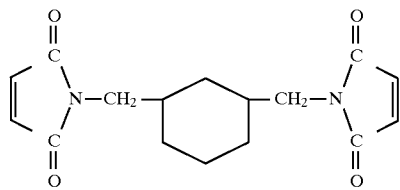

DETAILED DESCRIPTION OF THE INVENTION

The present novel bismaleimide compound can be readily produced by reaction of 1,3-bis(aminomethyl)cyclohexane with maleic anhydride. The reaction consists of two stages. First stage reaction is carried out generally by using one part by mole of 1,3-bis-(aminomethyl)cyclohexane and 2 parts by mole of maleic anhydride in a reaction solvent such as ketones, for example, acetone, methyl ethyl ketone, methyl isobutyl ketone, etc., or an aprotic polar solvent, for example, dimethyl formamide, dimethyl acetamide, etc. at a reaction temperature of about 0° to about 15° C. to form bismaleamic acid represented by the following formula as an intermediate product:

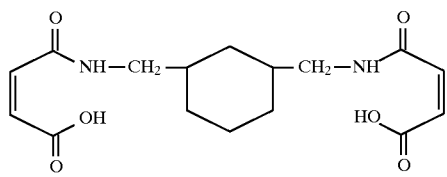

Second stage reaction is carried out generally at a reaction temperature of about 15° to about 50° C. for about 1 to about 3 hours by adding a basic catalyst such as triethylamine, etc. to the reaction mixture in a ratio of about 0.01 to about 0.1 by mole to the bismaleamic acid, without isolating the bismaleamic acid from the reaction mixture, and further adding a dehydrating agent such as acetic anhydride, etc. to the reaction mixture in a ratio of about 1 to about 3 by mole to the bismaleamic acid to form a bismaleimide compound as a dehydration-cyclization reaction product.

The bismaleimide compound thus obtained is soluble in acetone, methyl ethyl ketone, tetrahydrofuran, chloroform, dimethyl formamide, etc., where the compound of the following formula is soluble in dimethyl formamide, but slightly soluble in chloroform and insoluble in acetone, methyl ethyl ketone and tetrahydrofuran:

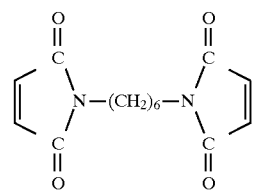

The compound having the following formula:

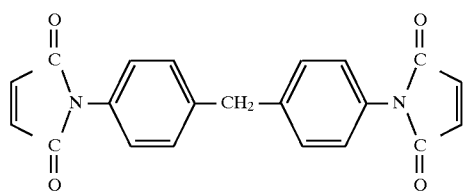

and the compound having the following formula:

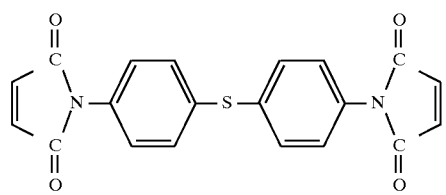

are both soluble only in dimethyl formamide, but are insoluble in acetone, methyl ethyl ketone, tetrahydrofuran and chloroform.

Bismaleimide compound can form polymaleimide resin through unsaturated bonds originating from the maleic anhydride groups. A varnish prepared by dissolving the polymaleimide resin in a low boiling point organic solvent such as methyl ethyl ketone, etc., when coated to a film of Kapton (trademark of polyimide resin made by Dupont, USA) and the film is applied and pressed to a copper foil, has a good adhesion, and thus can be used as an adhesive for FPC. Furthermore, the varnish, when applied to a copper foil and cured at a low temperature such as 200° C. for a short time such as 2 hours, can form an adhesive-free film of low dielectric constant. Furthermore, the varnish, when impregnated into fibers and dried, can form a prepreg as reinforced fibers. Laminated molding articles can be prepared from the prepregs by press molding or autoclave molding.

The present bismaleimide compound is soluble in a variety of ordinary low boiling point organic solvents up to a concentration of about 30 to about 40% by weight, and can provide good heat-resistant polymaleimide resin by heat polymerization thereof.

PREFERRED EMBODIMENTS OF THE INVENTION

The present invention will be described in detail below, referring to Example.

EXAMPLE 71 g (0.5 moles) of 1,3-bis(aminomethyl)cyclohexane and 284 g of methyl isobutyl ketone were charged into a seprable flask provided with a stirrer, a thermometer and a dropping funnel, and after dissolution of the former into the latter a solution containing 98 g (one mole) of maleic anhydride in 392 g of methyl isobutyl ketone was dropwise added thereto at room temperature, followed by stirring for one hour. Successively, 5 g (0.05 moles) of triethylamine and 51 g (0.5 moles) of acetic anhydride were added thereto, followed by stirring for 3 hours. After the reaction, the reaction mixture was thrown into water, and 142 g of precipitated crystals were recovered as a desired product (yield: 90%). The crystals had the following properties:

Melting point: 142° to 144° C.

$^1$H-NMR: 6.8 ppm (double bond of bismaleimide)

Infrared absorption spectra (KBr): 1710 cm$^{-1}$ (imide bond)

1760cm$^{-1}$ (imide bond)

What is claimed is:

1. A process for producing a bismaleimide compound comprising:

reacting 1,3-bis(aminomethyl)cyclohexane with maleic anhydride in methyl isobutyl ketone to form an intermediate reaction mixture containing bismaleamic acid as an intermediate reaction product;

adding a basic catalyst and a dehydrating agent to the intermediate reaction mixture; and then conducting a cyclization reaction to produce a final reaction mixture containing a bismaleimide compound having the following formula:

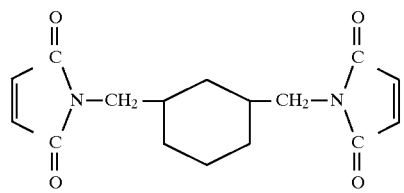

2. A process according to claim 1, wherein the basic catalyst is triethylamine.

3. A process according to claim 1, wherein the dehydrating agent is acetic anhydride.

4. The process for producing a bismaleimide compound according to claim 1 wherein the process further comprises the steps of:

adding the final reaction mixture to water; and then recovering precipitated crystals of the bismaleimide compound.

* * * * *